US 10,105,152 B2

United States Patent
Nikou et al.

(10) Patent No.: US 10,105,152 B2
(45) Date of Patent: Oct. 23, 2018

(54) SYSTEM AND METHODS FOR POSITIONING BONE CUT GUIDE

(71) Applicant: Blue Belt Technologies, Inc., Pittsburgh, PA (US)

(72) Inventors: Constantinos Nikou, Monroeville, PA (US); Branislav Jaramaz, Pittsburgh, PA (US); Barry Fell, Hummelstown, PA (US)

(73) Assignee: Blue Belt Technologies, Inc., Pittsburgh, PA (US)

( * ) Notice: Subject to any disclaimer, the term of this patent is extended or adjusted under 35 U.S.C. 154(b) by 0 days.

(21) Appl. No.: 15/248,914

(22) Filed: Aug. 26, 2016

(65) Prior Publication Data
US 2017/0007274 A1 Jan. 12, 2017

Related U.S. Application Data

(63) Continuation of application No. 14/634,422, filed on Feb. 27, 2015.
(Continued)

(51) Int. Cl.
*A61B 17/17* (2006.01)
*A61B 34/10* (2016.01)
(Continued)

(52) U.S. Cl.
CPC ........ *A61B 17/1764* (2013.01); *A61B 17/155* (2013.01); *A61B 17/157* (2013.01);
(Continued)

(58) Field of Classification Search
CPC ... A61B 17/17; A61B 17/1764; A61B 17/155; A61B 17/157
See application file for complete search history.

(56) References Cited

U.S. PATENT DOCUMENTS

| 4,759,350 A | 7/1988 | Dunn et al. |
| 4,841,975 A | 6/1989 | Woolson |

(Continued)

FOREIGN PATENT DOCUMENTS

| EP | 1669033 B1 | 2/2009 |
| WO | 2011106399 A1 | 9/2011 |

(Continued)

OTHER PUBLICATIONS

Chao et al. "Simulation and Animation of Musculosketal Joint System" (Nov. 1, 1993) J. Biomechanical Engineering 115(4B): 562-568.

(Continued)

*Primary Examiner* — Christopher Beccia
(74) *Attorney, Agent, or Firm* — Pepper Hamilton LLP

(57) ABSTRACT

Examples of an orthopedic surgical device for use in operating on a target bone and methods for operating a system for use in orthopedic surgery on a bone are generally described herein. An orthopedic surgical device can include an primary positioning block, and a secondary positioning component removably coupled to the primary positioning block. The secondary positioning component can be configured to: engage a prepared engagement feature machined into the target bone, and guide the primary positioning block to a predetermined position on a target bone. The orthopedic surgical device can include a first cutting block configured to: removably couple to the primary positioning block, and guide a cutting tool to cut the target bone.

20 Claims, 7 Drawing Sheets

Related U.S. Application Data

(60) Provisional application No. 62/119,901, filed on Feb. 24, 2015, provisional application No. 61/946,428, filed on Feb. 28, 2014.

(51) Int. Cl.
  *A61B 34/20* (2016.01)
  *A61B 17/15* (2006.01)

(52) U.S. Cl.
  CPC ............. *A61B 34/10* (2016.02); *A61B 34/20* (2016.02); *A61B 2034/104* (2016.02); *A61B 2034/105* (2016.02); *A61B 2034/107* (2016.02); *A61B 2034/108* (2016.02)

(56) References Cited

U.S. PATENT DOCUMENTS

| | | |
|---|---|---|
| 4,979,949 A | 12/1990 | Matsen, III |
| 5,086,401 A | 2/1992 | Glassman |
| 5,129,909 A | 7/1992 | Sutherland |
| 5,186,174 A | 2/1993 | Schlondorff et al. |
| 5,344,423 A | 9/1994 | Dietz et al. |
| 5,408,409 A | 4/1995 | Glassman et al. |
| 5,474,559 A | 12/1995 | Bertin et al. |
| 5,494,034 A | 2/1996 | Schlondorff et al. |
| 5,496,324 A | 3/1996 | Barnes |
| 5,514,139 A | 5/1996 | Goldstein et al. |
| 5,571,110 A | 11/1996 | Matsen, III et al. |
| 5,682,886 A | 11/1997 | Delp et al. |
| 5,824,085 A | 10/1998 | Sahay et al. |
| 5,880,976 A | 3/1999 | DiGioia, III et al. |
| 5,916,220 A | 6/1999 | Masini |
| 6,205,411 B1 | 3/2001 | DiGioia, III et al. |
| 6,757,582 B2 | 6/2004 | Brisson |
| 7,608,079 B1 | 10/2009 | Blackwell et al. |
| 7,747,311 B2 | 6/2010 | Quaid, III |
| 7,857,821 B2 | 12/2010 | Couture et al. |
| 8,282,646 B2 | 10/2012 | Schoenefeld et al. |
| 8,425,524 B2 | 4/2013 | Aker et al. |
| 9,386,994 B2 | 7/2016 | Agnihotri et al. |
| 9,414,846 B2 | 8/2016 | Gillman et al. |
| 9,585,725 B2 | 3/2017 | Bonutti |
| 9,717,510 B2 | 8/2017 | Smith |
| 9,782,261 B2 | 10/2017 | Collazo et al. |
| 9,827,115 B2 | 11/2017 | Walker et al. |
| 9,839,531 B2 | 12/2017 | Netravali et al. |
| 9,855,106 B2 | 1/2018 | Jaramaz et al. |
| 9,872,733 B2 | 1/2018 | Shoham et al. |
| 2004/0128026 A1 | 7/2004 | Harris et al. |
| 2005/0149041 A1 | 7/2005 | McGinley et al. |
| 2005/0171545 A1 | 8/2005 | Walsh et al. |
| 2005/0234465 A1 | 10/2005 | McCombs et al. |
| 2006/0030853 A1 | 2/2006 | Haines |
| 2006/0122617 A1 | 6/2006 | Lavallee et al. |
| 2006/0195111 A1* | 8/2006 | Couture ................. A61B 17/15 606/86 R |
| 2006/0200163 A1 | 9/2006 | Roger et al. |
| 2007/0239153 A1 | 10/2007 | Hodorek et al. |
| 2007/0249967 A1* | 10/2007 | Buly .................... A61B 5/1121 600/595 |
| 2008/0154269 A1 | 6/2008 | Roger et al. |
| 2009/0082774 A1 | 3/2009 | Oti et al. |
| 2009/0131941 A1* | 5/2009 | Park .................... A61B 17/154 606/87 |
| 2009/0287222 A1 | 11/2009 | Lee et al. |
| 2010/0100192 A1 | 4/2010 | Haines et al. |
| 2010/0191244 A1 | 7/2010 | White et al. |
| 2011/0112542 A1 | 5/2011 | Gross |
| 2011/0130761 A1 | 6/2011 | Plaskos et al. |
| 2011/0245835 A1* | 10/2011 | Dodds .................. A61B 17/155 606/87 |
| 2011/0257653 A1 | 10/2011 | Hughes et al. |
| 2012/0078254 A1 | 3/2012 | Ashby et al. |
| 2012/0078263 A1 | 3/2012 | Parisi et al. |
| 2012/0220859 A1 | 8/2012 | Amiot et al. |
| 2012/0323244 A1 | 12/2012 | Cheal et al. |
| 2013/0172905 A1 | 7/2013 | Iorgulescu et al. |
| 2013/0317523 A1 | 11/2013 | Borus |
| 2014/0243833 A1* | 8/2014 | Smith ................ A61B 17/1626 606/87 |
| 2014/0257293 A1 | 9/2014 | Axelson, Jr. et al. |
| 2015/0057758 A1 | 2/2015 | Axelson, Jr. et al. |
| 2016/0030063 A1 | 2/2016 | Pack et al. |
| 2016/0045268 A1 | 2/2016 | Keppler et al. |
| 2016/0374693 A1 | 12/2016 | Van Citters et al. |
| 2017/0007331 A1 | 1/2017 | Couture et al. |
| 2017/0014189 A1 | 1/2017 | Jaramaz et al. |

FOREIGN PATENT DOCUMENTS

| | | |
|---|---|---|
| WO | 2013136303 A1 | 9/2013 |
| WO | 2015131133 A1 | 9/2015 |
| WO | 2015131138 A1 | 9/2015 |

OTHER PUBLICATIONS

Chinese Office Action for CN20130058810.6 dated Feb. 6, 2017.
Chinese Office Action for CN201480027135.5 dated Jan. 17, 2017.
Delp et al. "An Interactive Graphics-Based Model of the Lower Extremity to Study Orthopaedic Surgical Procedures" (Aug. 1990) IEE Transactions on Biomedical Engineering 37(8): 757-767.
DiGioia et al. "An Integrated Approach to Medical Robotics and Computer Assisted Surgery in Orthopaedics" (1995) Carnegie Mellon University 106-111.
DiGioia et al. "HipNav: Pre-operative Planning and Intra-operative Navigational Guidance for Acetabular Implant Placement in Total Hip Replacement Surgery" (Nov. 1995) Preceedings of CAOS '96 1-8.
Harris et al. "Experiences with Robotic Systems for Knee Surgery" (Mar. 19-22, 1997) Springer-Verlag, London, UK 757-766.
Freysinger et al. "A Passive-Marker-Based Optical System for Computer-Aided Surgery in Otorhinolaryngology: Development and First Clinical Experiences" (Feb. 2002) The Laryngoscope 112(2):409.
O'Toole III et al. "Towards More Capable and Less Invasive Robotic Surgery in Orthopaedics" (1995) Computer Vision, Virtual Reality and Robotics in Medicine 905: 123-130.
Taylor et al. "An Image-Directed Robotic System for Precise Orthopaedic Surgery" (Jun. 1994) IEE Transactions on Robotics and Automation 10 (3): 261-275.
Roccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.
Dillman et al. "Haptic Devices in Medical Applications" (Jun. 23, 1999) Institute for Process Control and Robotics, 1st International rkshop, Paris, France, pp. 12-22.
International Search Report and Written Opinion for PCT/US2015/018161 dated May 27, 2015.
International Search Report and Written Opinion for PCT/US2015/018155 dated May 27, 2015.
Extended European Search Report dated Oct. 19, 2017 for corresponding European Patent Application No. 15755754.7.

* cited by examiner

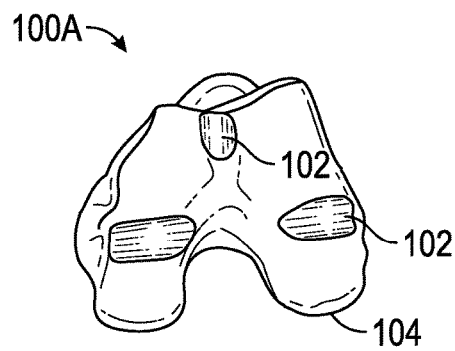
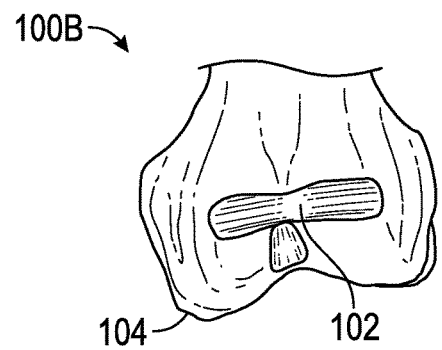
FIG. 1A  FIG. 1B
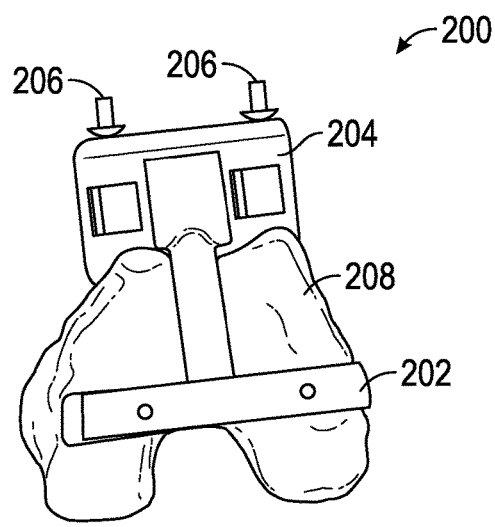
FIG. 2

SYSTEM AND METHODS FOR POSITIONING BONE CUT GUIDE

CLAIM OF PRIORITY

This patent application claims the benefit of priority of U.S. Provisional Patent Application Ser. No. 61/946,428, titled "System and Methods for Positioning Bone Cut Guide," filed on Feb. 28, 2014, which is hereby incorporated by reference herein in its entirety.

This patent application claims the benefit of priority of U.S. Provisional Patent Application Ser. No. 62/119,901, titled "System and Methods for Positioning Bone Cut Guide," filed on Feb. 24, 2015, which is hereby incorporated by reference herein in its entirety.

TECHNICAL FIELD

This document relates generally to computer-aided orthopedic surgery, and more specifically to systems and methods for positioning a cut guide to a target bone and for altering the target bone using the cut guide.

BACKGROUND

The use of computers, robotics, and imaging to aid orthopedic surgery is well known in the art. There has been a great deal of study and development of computer-aided navigation and robotics systems used to guide surgical procedures. For example, a precision freehand sculptor (PFS) employs a robotic surgery system to assist the surgeon in accurately cutting a bone into a desired shape. In interventions such as total hip replacement, computer-aided surgery techniques have been used to improve the accuracy, reliability of the surgery. Orthopedic surgery guided by images has also been found useful in preplanning and guiding the correct anatomical position of displaced bone fragments in fractures, allowing a good fixation by osteosynthesis.

A cut guide can be used in an orthopedic surgery to assist a surgeon in cutting or modifying some portions of a target bone. For example, in joint replacement surgeries such as total hip replacement (THR) or total knee replacement (TKR), a cut guide can be temporarily attached to the target bone such as a femur or a tibia. An orthopedic surgical cutting tool can be used together with the cut guide to allow the surgeon to selectively cut portions of the ends of the target bone and replaced with endoprosthetic implants. Positioning a cut guide for use in preparing the target bone can be a time consuming and complicated process, which is critical to positive outcomes for the patient.

SUMMARY

Quick and reliable positioning of a cut guide can be crucial to the outcome of orthopedic surgeries such as prosthesis implantation. In joint replacement surgeries, for example, portions of the articulation tissues of a target bone, such as acetabulum, a femur, or a tibia, need to be resected and altered to allow an implant to be securely positioned onto the target bone. A cut guide positioned on the target bone can be used to guide a cutting saw to resect the target bone to a desired shape. Proper positioning of the cut guide on the bone can improve the accuracy of the bone resection and reduce procedure time. On the contrary, improper positioning of the cut guide can result in undesirable cutting surfaces on the target bone, which can further cause impingement, increased rates of implant dislocation, wear and failure of the implant, among many other complications. The procedure time can also be lengthened due to the requirement of modifying the undesirable cutting shape.

Positioning of cut guide onto a target bone usually requires a surgeon to mentally map and compare the shape, orientation, and relative positions of the implant and the target bones. This method can be difficult to operate and can suffer from lack of reliability and certainty. Determining and visualizing the correct positions and orientations of the prosthesis with respect to the target bone can be practically difficult. Computer-aided tools can be used to assist the surgeon in positioning the cut guide relative to the bone. However, often the computer-assistance is limited to intra-operative navigation of traditional cutting jigs. The designs of these jigs, the tools to align them, and the implants that they support are all compromises meant to serve a general population. Other systems uses computers to analyze patient specific images used to design patient-conforming instrumentation and sometimes even implants specific to the patient. However, these images either use ionizing radiation (e.g. computed tomography images) or are prone to error or gaps in tissue differentiation (e.g. magnetic resonance imaging). Therefore, the present inventors have recognized that there remains a considerable need for systems and methods that can assist the surgeon in reliably positioning a cut guide onto the target bone with improved accuracy, speed, and consistency, while still allowing for some customization for patient specific differences.

Various embodiments described herein can, among other things, help improve the efficacy and the reliability in positioning a cut guide onto a target bone to alter a portion of the target bone. For example, an orthopedic surgical device can comprise a primary positioning block. The orthopedic surgical device can comprise a secondary positioning component removably coupled to the primary positioning block, the secondary positioning component configured to: engage a prepared engagement feature machined into the target bone, and guide the primary positioning block to a predetermined position on a target bone. The orthopedic surgical device can comprise a first cutting block configured to: removably couple to the primary positioning block, and guide a cutting tool to cut the target bone.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 1A-B illustrate generally prepared engagement features, in accordance with some examples.

FIG. 2 illustrates generally an anterior distal positioning fixture in accordance with some examples.

DETAILED DESCRIPTION

Figure 3A:
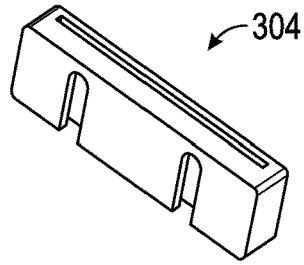
FIGS. 3A-D illustrate generally distal cutting block systems in accordance with some examples.

Total knee replacement surgery requires several precise cuts to be made in the femur and tibia in order for the chosen implant to fit correctly and to restore the geometry and kinematics of a natural healthy knee. To perform these steps, in both conventional (manual method) and Computer Aided Surgery (CAS) total knee replacement, a series of guide blocks are used that provide a drill or cutting guide to assist the surgeon to perform the steps required to prepare the femur and tibia for receiving the implant.

The conventional manual instrumented method used to prepare the femur for a knee replacement implant, outlined below as an example, generally includes fastening a distal cutting guide block on the femur, generally located by an intramedullary pin (IM rod) or screw inserted into the distal end of the femur and locating the distal guide block in the desired position, such position providing correct implant varus-valgus and transverse rotational angle about the IM rod and proper amount of distal resection; aligning a distal cutting guide, whether being integral with the guide block or a separate element fastenable thereto, in a predetermined location relative to the distal guide block reference position and inserting locating pins through the distal cutting guide and into the femoral condyles to fasten the cutting guide in place on the anterior surface; making the distal cut to resect the predetermined amount of bone from the distal end of the condyles; positioning a second femoral implant sizing guide (the femoral sizer) freely on the newly cut distal surface of the femur and ensuring that the anticipated resection level for the anterior cut, the anterior-posterior adjustment (referencing off either the existing posterior condyle or the anterior femur) for correct implant sizing, and that the rotational alignment and medial-lateral position of the positioning block are all correct before fixing the 4-in-1 cutting guide block in place with pins, drilling the implant peg holes; and performing the anterior and posterior cuts, and subsequently make the anterior-posterior chamfer and notch cuts. Note that adjusting rotation of the implant in the sagittal plane is generally not possible with the IM rod based instruments typically in use today. Thus, a femoral implant's position in knee extension is normally set parallel to the IM rod axis.

The steps required to prepare the tibia are less involved. Generally, they include: aligning the mechanical axis of the tibia; obtaining proper rotational (varus-valgus) alignment of the guide block, and fastening it in place to the anterior surface of the proximal end of the tibia; adjusting the vertical and angular position of the tibial guide block to ensure that the desired posterior slope and level of tibial resection are provided; inserting location pins using the guide block to fix its position on the tibia; removing the guide block and replacing it with a tibial resection cutting guide that is retained in place with the location pins; and resecting the chosen amount of tibial bone. Note that the final position of the tibial plate implant is not determined by this step, only the planar surface on which it will rest. Anterior-posterior (AP), medial-lateral (ML), and rotational positioning of the tibial plate implant are subsequently determined by the surgeon's judgment as to its best fitting location on the resected tibia after the femoral implant has been located and fixed to the resected femur.

The above described surgical procedure remains generally similar whether traditional or computer assisted surgery is being performed. A CAS system can employ passive or active trackable elements affixed to surgical tools and patient bone references, to permit the determination of position and orientation of the these objects in three-dimensional space. In certain types of CAS, preoperatively taken images or computer generated models created from preoperative patient scans, can be used to provide accurate patient specific anatomical information. The images or models can be used to registered or calibrate real-time position of the same patient's anatomical elements. This can permit subsequent tracking of the patient's anatomical elements and display of these anatomical elements relative to the surgical tools used during the surgery.

The use of a cutting/drill-positioning block having a position-identifying member, such as tracker assemblies, fastenable thereto and trackable by a camera based CAS system, for example, can be used in total knee replacement surgery. While such tracked femoral positioning guide blocks can provide significant advantages over traditional non-CAS instruments, the use of the CAS often leads to longer surgical times.

As discussed above, total knee replacement procedures can include the same step-wise method of creating the necessary cuts on the femur in order to resect enough bone to permit the installation of the femoral implant. In conventional, or non-computer assisted, total knee replacement surgery, a distal cutting block is positioned and aligned by the surgeon and pinned in place on the anterior surface of the femur such that the cutting slot is aligned in the correct location for the distal cut. In CAS total knee replacement, the CAS navigation locates the distal pin drill guide position on the femur to accurately create the pin holes into which locating pins are inserted and employed to eventually fix the distal cutting guide. Generally, the distal drill/cutting guide member comprises part of an assembly, including an anterior guiding platform, that is fixed relative to the femur and on which the drill/cutting guide is displaceable proximally by a selected, measurable amount to locate the drill/cutting guide in a desired position relative to the anterior guiding platform and therefore relative to the distal end of the femur. A tracked guide block can be intramedullarly fastened to the femur, and the anterior guiding platform can engage with the tracked guide block. Depending on the type of implant being used, and once aligned with the most distal femoral condyle, the drill/cutting guide can be proximally displaced from the normal joint line on the fixed anterior guiding platform by a selected amount, corresponding to the amount of bone to be resected for the particular implant being used.

The use of CAS can improve the location of implant cutting guides, and by integrated reference, the implant location on the bone but generally, the use of CAS in previous procedures has not changed the basic method and sequence of performing the bone preparation.

Recently, an alternative CAS system that employs a pre-operative scanning procedure, typically a CT or a MRI, has been successfully demonstrated. The system provides shape based recognition of the bone and, by planning the desired implant location, is able to provide a fabricated, patient-specific cutting jig and a patient-specific implant device whose components can be aligned and altered by the physician prior to manufacturing, according to the specific patient's requirements and the physician's preference.

A primary feature of this method is the use of pre-procedure imaging of the involved joint. The system software, typically provided as a service to the physician, calculates the geometrical information on the damaged bone, captured in CT or another suitable imaging format, and converts this information into a three-dimensional (3D) model of the bone surfaces. The converted 3D model includes information on corresponding bone dimensions. The surgeon, using the CAS, determines a femoral mechanical axis (FMA), femoral mechanical center (FMC), femoral anatomical axis (FAA) and tibial mechanical axis (TMA), and decides how and where the implant components should be placed on the bones of the particular patient. Once the planning is complete, the system software prepares and provides a computer file to direct rapid production machines, such as a computer numerical control (CNC) machine, a 3D printer machine, etc., to fabricate a patient specific, disposable cutting jig or a cutting guide device. The cutting jig and implant device can include a surface profile that matches the patient's bone surfaces in vivo, as predicted by the pre-procedure imaging scan, and can cause a specific fit of the cutting jig to only one position on the patient's knee.

Referencing to the geometry of the cutting jig surface profile, guiding holes for drilling and inspection, a slot feature for a sawing process, and bushing features for reaming and drilling can be fabricated into the cutting jig. During surgery, the patient specific cutting jig is fitted onto the predetermined location on the bone to guide critical cuts and shaping of the bone, such as drilling, reaming, sawing, etc., thus ensuring the surgeon's pre-determined and desired location of the implant on the patient's knee.

The above described CAS system uses a computer-aided calibration process that matches the surface of the cutting jig or implant device to the bone surface(s). Because the cutting jig or implant device is fabricated using CT scan image data, there is no need for use of a registration process, tracking systems or robotic systems in the operating room. The CAS system thus is designed to work in conjunction with manual standard TKA instrumentation and the cutting jig or implant device can provide a reduction in surgical time. However, the CAS system above requires the additional expense of the pre-procedure imaging scan as well as the time and cost for physician review, fabrication, sterilization, packaging and delivery of the patient specific cutting jig to the operating room. Additionally, the patient specific cutting jig is only suitable for the distal femoral cut and tibial cut. The 4-in-1 cutting block must still be placed for those cuts after the distal cut has been made. While the above CAS system can eliminate the use of the IM rod, during surgery, it has been found that the patient specific instrumentation (e.g., cutting jig) often does not fit well with the patient's anatomy, revealing a limitation of the accuracy of pre-procedure imaging technique. Adjustments to the patient's anatomy then must be made to ensure proper fitting, and this introduces the possibility of implant positioning errors.

The previously described systems used in total knee replacement surgery are still lacking in capability, accuracy, and efficiency of timely placement.

In an example, a computer controlled surgical instrument can be used in combination with an anatomical navigation system to place, size and locate specific machined areas onto the bone that will then unambiguously mate with size specific, non-patient specific, instrumentation. Such equipment can include, for example, the NAVIO® Surgical System from Blue Belt Technologies, RIO robotic arm interactive orthopedic system from Mako Surgical, daVinci Surgical System from Intuitive Surgical, and other similar systems. The NAVIO® system can be used effectively because its navigation component does not require pre-imaging of the patient and instead uses a navigated stylus to determine actual patient anatomic features in conjunction with fixed bone landmarks such as the femur and tibia. Systems and methods to use the NAVIO® system are described in U.S. Pat. No. 6,757,582, titled "Methods and Systems to Control a Shaping Tool" to Brisson, et.al, which is hereby incorporated by reference herein in its entirety.

In an example, a database of implant sizes is contained in CAS navigational software. A surgeon, having fully mapped all of the key anatomical landmarks, can use the CAS system, in the example of a total or partial knee replacement, to calculate a femoral mechanical axis (FMA), femoral mechanical center (FMC), femoral anatomical axis (FAA) and tibial mechanical axis (TMA). With this compiled data, which is specific to the particular patient, the surgeon can use the planning aspect of the CAS software to position the articulating surface of the implants in virtual space and confirm, through range of motion of the actual joint, that the implant selection and positioning of the articulating surfaces is correct. Systems and methods to use a CAS system are described in U.S. Provisional Patent Application Ser. No. 61/948,102, titled "Computer-aided Prosthesis Alignment," filed on Mar. 5, 2014, which is hereby incorporated by reference herein in its entirety.

At this point in the procedure, a typical CAS system would require the use of cutting guides and instruments that are capable of interacting with the CAS system, in order to be properly placed in preparation of making the final bone cuts. Alternatively, the MAKO system uses a robot arm to hold the cutting blocks in place, in proper relation to the bone about to be cut. In either case, once the planning step has finished, the next step for the surgeon is to fix the cutting guides in place, their position determined by the location of the articulating surfaces, relating them to the selected implant backside surface geometry, confirming the required bone resection for the particular implant size and then performing the bone cuts, a step that when completed, does not allow for any subsequent change in implant position, even if it is incorrect, due to poor or inadequate planning by the physician.

In an example, the system described herein can improve the previously described systems for performing the surgery, and can allow for more interaction and confirmatory steps by the physician to help assure proper placement of the implant. For example, after virtual placement of the implant in the CAS system, instead of going directly to the positioning of the navigated cutting blocks, a system can use a navigated, controlled instrument (burr) of the NAVIO® system to place a series of shallow burred areas (e.g., zones or engagement features) at specific locations on the bone that can provide for the specific location of the provided instruments on the bone, without the need for the instruments themselves to be navigated. Along with the implant database that is part of the CAS system, the database also can include additional information that relates specific locations on the backside of the implant with articulating surfaces. The combination of this system and additional implant data can allow the surgeon to make confirmatory judgment of the final implant position before irreversible bone resection has occurred. In another example, the system can allow for all of the bone cuts to be made using the combination of the navigated cutting zones and the generic instruments. This combination allows the CAS system to create a patient specific placement of the implants without the need for pre-imaging or the need for expensive, navigation capable instruments or expensive robotic arms. U.S. Provisional Patent Application Ser. No. 61/946,428, titled "System and Methods for Positioning Bone Cut Guide," filed on Feb. 28, 2014, is hereby incorporated by reference herein in its entirety.

A method for operating on a target bone can include using a CAS system to determine a femoral mechanical axis (FMA), femoral mechanical center (FMC), femoral anatomical axis (FAA) and tibial mechanical axis (TMA) with typical fixed bone navigation trackers/markers and navigation methods. A navigated stylus can be used to record actual (patient specific) bone and articular surfaces such as the position, width or shape of the posterior condyles, width or shape of the distal condyle, width or position of the trochlear groove and sulcus on the anterior femur, width, slope, relative depth of the tibial plateau or position or shape of any eburnated bone on the tibial plateau or femoral condyle, or "Whiteside's line". An implant can be virtually placed onto the bone and fitted for best size match, desired extension and flexion gap, varus-valgus alignment, distal position on the femur, proximal position on the tibia, matching of posterior, distal and sulcus articular surfaces with those of the femoral implant, rotation in the sagittal plane of the femoral implant or posterior slope of the tibial implant, or internal-external rotation of the implants.

In an example, since the implant geometry, specifically the femoral and polyethylene insert implant articulating surfaces, can be known to the CAS system via a database, the ML, AP, and rotation of the tibial components (tibial plate and polyethylene insert) can be aligned on the resected tibia to a best fit position relative to the femoral implant. This can avoid creating a mismatch of the femoral and tibial components during ambulation.

After the virtual implant has been sized to the patient's anatomy, the computer can create virtual burr zones on the patient's joint surfaces that represent a typical (e.g., 3-4 mm) offset from the backside of the selected femoral and tibial implant at specific locations of the implant. These specific locations can include the midpoint (AP) of the distal cut surface, the vertex of the anterior chamfer and anterior cuts, along the deepest portion of the implant's trochlear groove, the distal surface of the tibial implant or other aspects of the tibial cutting guide.

FIGS. 1A-B illustrate generally prepared engagement features (e.g., 102), in accordance with some examples. In an example, for a femoral implant, after the regions for burring have been set virtually, the NAVIO® system, or other CAS system, can control the cutting action of the engagement features (burrs) 102 and allow cutting in the zones identified (e.g., the burr zones). For example, a virtual model of the engagement features 102 on the bone 104 can be made and then cuts can be done as shown in views 100A and 100B. In an example, view 100A includes a view of the bone 104 and engagement features 102 from front view and view 100B includes a view of the bone 104 and engagement features 102 from a top view. The engagement features 102 can be cut into the bone 104 to provide burr zones for accepting a distal positioning component of an anterior distal positioning fixture. In an example, a system can include two or more engagement features to receive a positioning component or components. For example, four engagement features can be used to receive a distal positioning component of an anterior distal positioning fixture.

A distal cut can be performed first as this burr zone can be located in such a manner that it is independent of final implant size selection. The surgeon can make this burr first on the most involved (degenerated) compartment (medial or lateral condyle) and see if adequate bone removal has been planned in the CAS system. He can also check the ML width of the implant selection with the provided size specific instruments. If adjustments need to be made, the surgeon can virtually move the implant (e.g., more or less proximal, ML rotation, AP rotation, etc.) in the CAS planning software and the other, remaining burr cuts can be adjusted accordingly.

Once the surgeon is satisfied with the implant size, the anterior bone resection location can be determined. For example, the location can be where the implant will merge with the anterior femur. The location can be determined with respect to determining if too much notching of the anterior femur will occur. In an example, since the instrument system is not tied to an IM rod based method, the femoral implant can be rotated in the sagittal plane to accommodate a different size and still make sure that the posterior positioning of the implant matches the patient's articular surfaces.

In an example, the medial-lateral position can be adjusted to provide a best match with the overall femoral width. In another example, the internal or external rotation can be adjusted so the implant's sulcus matches the patient's existing Whiteside's line (sulcus/trochlear groove) location. These adjustments can match the implant's trochlear groove with the patient's patella tracking Once all of the implant positional adjustments are made, the anterior and sulcus burr zones can be finished.

FIG. 2 illustrates generally an anterior distal positioning fixture 200 in accordance with some examples. The placement of burred cuts (e.g., engagement features 102 from FIG. 1) can allow for location specific positioning of a size-specific fixture. With placement of a size-specific Anterior/Distal Positioning Fixture 200 (ADPF), implant size, proper distal cut depth, AP position, ML position, or proper anterior flange width/depth can be confirmed. The confirmation of implant positioning or size is not possible at this point in a typical TKR procedure since significant bone resection has not yet occurred. Position of the ADPF 200 can be fixed with the placement of two or more headed screws or pins (e.g., screws 206) into the anterior femur (e.g., bone 208).

In an example, the ADPF 200 can be placed on the bone 208. A distal positioning component 202 of the ADPF 200 can be set in the burr zones (e.g., the engagement features of FIG. 1). The distal positioning component 202 can be used to set a position for an anterior positioning block 204 of the ADPF 200. A distal positioning component can include a specific example of a secondary positioning component and an anterior positioning block can include a specific example of a primary positioning block. The distal positioning component 202 can be removed after screws 206 are added to the anterior positioning block 204. In an example, the burr zones (e.g., engagement features 102 of FIG. 1) are determined using a CAS system, then cut into the bone 208. The distal positioning component 202 can be placed on the bone 208 in a position determined by the CAS system using the engagement features. The distal positioning component 202 can be used as a guide to properly place the anterior positioning block 204. The anterior positioning block 204 can be used to place other cutting components to cut the bone 208. The engagement features or burr zones can be cut into the bone 208 in unobtrusive areas on the bone 208, (e.g., areas that do not affect functioning of the bone 208, areas that will be cut again later, areas that do not cause pain, etc.). Using the distal positioning component 202 to guide the anterior positioning block 204 can allow for more accurate placement of the anterior positioning block 204 on the bone 208 or allow for the burr zones or engagement features to be placed in unobtrusive areas.

Figure 3B:
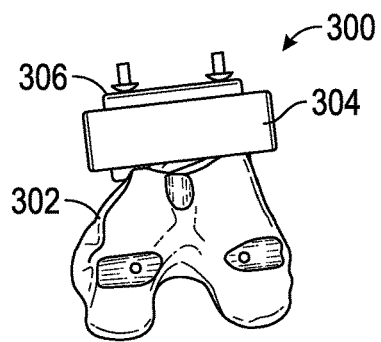

FIGS. 3A-D illustrate generally a distal cutting block systems (e.g., 300, 301, or 303) in accordance with some examples. In an example, a general cutting block can include a first cutting block or a distal cutting block. In an example, FIG. 3A shows a distal cutting block 304. FIG. 3B shows the distal cutting block 204 in a distal cutting block system 300. In an example, the distal cutting block system 300 of FIG. 3B includes an anterior cutting block 306 (e.g., the anterior positioning block 204 that was placed in FIG. 2 by the distal positioning component 202) and a bone 302. The distal cutting block 304 can be placed in a position relative to the bone 302 that overlaps with a position for a distal positioning component used to place the anterior positioning block 304. For example, a distal positioning component can be used to place the anterior positioning block 304 and then be removed followed by placement of the distal cutting block 306 placed as shown in FIG. 3B. The distal cutting block 306 can be used to make a distal cut, as shown in distal cutting block system 301 in FIG. 3C.

Figure 3C:
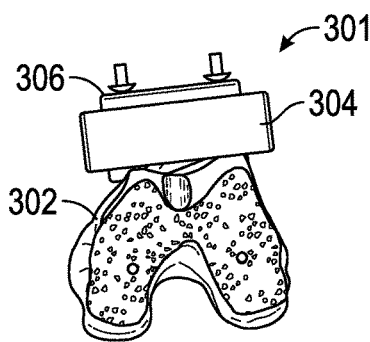
Figure 3D:
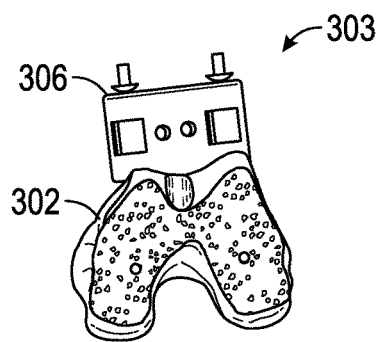

In an example, after a distal positioning component is removed, a distal cutting block 306 can be attached to the remaining anterior positioning block 304. A distal cut can be made using the distal cutting block 306. The distal cutting block 306 can be removed after the distal cut is made, as shown in distal cutting block system 303 in FIG. 3D. The anterior positioning block 304 can remain in place. In an example, as shown in FIGS. 3C and 3D, the distal cutting block 306 can be used to make a distal cut that removes areas around engagement features on the bone.

Figure 4A:
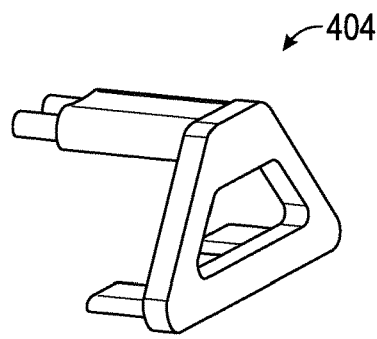
FIGS. 4A-B illustrate generally a universal adapter and a 4-in-1 cutting block in accordance with some examples.
Figure 4B:
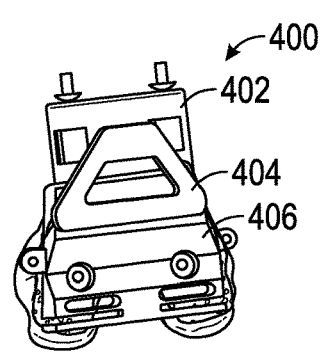

FIGS. 4A-B illustrate generally a universal adapter 404 and a 4-in-1 cutting block 406 in accordance with some examples. FIG. 4A shows a universal adapter 404 that can be used in cutting block system 400 in FIG. 4B. The universal adapter 404 can be used to attach the 4-in-1 cutting block 406 to the anterior positioning block 402 as shown in FIG. 4B. With the use of the universal adapter 404, a standard 4-in-1 cutting block (e.g., 4-in-1 cutting block 406) can be attached to the anterior positioning block 402. In an example, a femoral peg hole location can be done prior to attaching the 4-in-1 cutting block 406. In another example, the surgeon can fine tune the ML positioning of the implant at this point using the cutting block system 400. In an example, the universal adapter 404 assists the surgeon in positioning the 4-in-1 cutting block 406, while allowing for adjustment in the ML positioning by sliding the 4-in-1 cutting block along a slot in the proximal surface that mates with tabs on the universal adapter 404. The 4-in-1 cutting block 406 can be attached with screws or pins through peg hole locators or wing pinholes. For example, the distal positioning component and the 4-in-1 cutting block can re-use holes on the bone for attaching to the bone.

In an example, connecting a component or block to a bone using holes on the bone or the component can cause positive engagement of the component or block with the bone. This can improve accuracy of subsequent bone cuts. For example, a component or block can be loosely fitted to a bone and then tightened to an accurate engagement position by screwing or pinning the component or block to the bone.

The anterior positioning block 402 and the universal adapter 404 can be removed after the 4-in-1 cutting block 406 is secure or attached. In an example, the universal adapter 404 or 4-in-1 cutting block 406 can be positioned relative to the bone in positions that overlap a portion of one or more of the areas previously occupied by the distal cutting block or the distal positioning component. For example, two or more of the distal cutting block, distal positioning component, universal adapter, or 4-in-1 cutting block 406 can attach to a same face of the anterior positioning block 402.

In another example, the femur can be prepared using navigated holes that can result in further substantial time-savings. By using the navigated holes, steps can be eliminated from a standard procedure, including use of the traditional IM distal cut apparatus, use of the femoral sizer apparatus, or determination of the cutting position blocks location.

In yet another example, the methods and systems described can be used in a minimally invasive surgery (MIS) total knee replacement (TKR). For example, a positioning block or positioning component can include a medial or lateral positioning block or positioning component. A positioning block or component can be designed for use in a MIS TKR or can be used without modification from those used for a typical TKR. The MIS TKR can include a positioning block or component used to avoid muscle (e.g., muscle sparing) or when using minimal arthrotomy length. In non-typical, non-MIS, procedures, devices, components, blocks, etc., described herein can be modified for use in special circumstances. For example, if everted patella or typical arthrotomy length are not present in a procedure, one or more of the components, blocks, devices, cuts, etc., can be modified to aid in surgery.

Various components, blocks, devices, instruments, etc., described herein can be re-used or be disposable after one use. For example, one or more of an anterior positioning block, distal positioning component, distal cutting block, 4-in-1 cutting block, universal adapter, tibial cutting block, tibial plate trial, or navigation positioner can be disposable and used only once, or can be re-used. In an example, one or more of the components, blocks, etc., described herein can include a material that allows for deformation. For example, a component or block can be made with a spring-like material (e.g., rubber, plastic, etc.) that allows a positive engagement with a bone via bending displacement. In an example, a component or block can be manufactured or fabricated as a single, unitary component or block. In another example, a component or block can be manufactured or fabricated in parts (e.g., two parts combined to make a component or block). Manufacturing or fabricating a tibial component in parts can facilitate a positive or locking connection to a bone. Manufacturing or fabricating can include traditional manufacturing, 3D printing, sculpting, etc.

In an example, additional operating room (OR) time that might be added by the use of a navigation procedure can be made up by use of the NAVIO® optimized instruments. The methods and systems described herein can include a "Patient Specific" knee implantation without using pre-procedure imaging or patient specific cutting guides or patient specific implants.

Figures 5A, 5B:
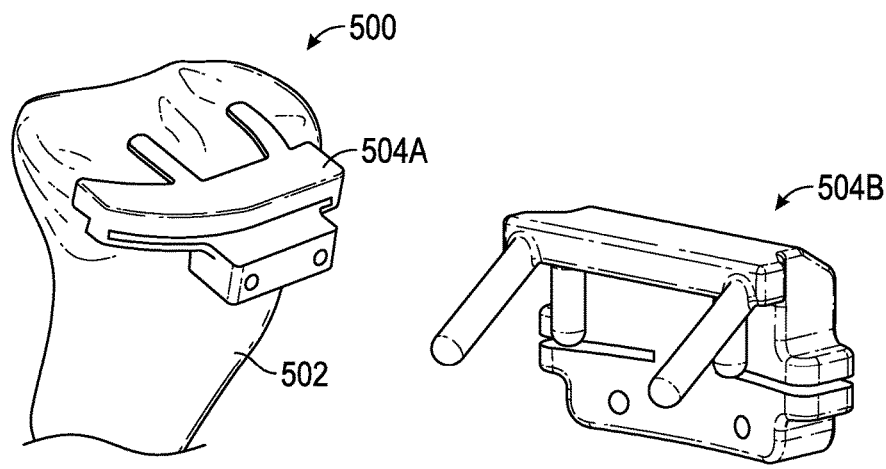
FIGS. 5A-B illustrate generally a tibial cutting block in accordance with some examples.

FIGS. 5A-B illustrate generally a tibial cutting block (e.g., 504A or 504B) in accordance with some examples. In an example, tibial preparations can be done in a similar manner to the methods and using the systems as described above for a femur (or other bone). For tibial preparations, an implant can be pre-positioned using the NAVIO® Software during a planning phase. Using the NAVIO® software, a cutting plane can be determined using a best-fit implant size and position.

In an example, the NAVIO® system can determine simple burred regions (e.g., three (3) or four (4) burr regions or zones—creating engagement features on the tibia) of the bone 502 that provide a correct posterior slope angle for the location of a tibial cutting block (e.g., 504A or 504B). A single left (L) or right (R) cutter can be used for any size implants. As shown in FIG. 5A, tibial cutting system 500 can inlcude the bone 502 (e.g., tibia) and the tibial cutting block 504A. Other versions of a tibial cutting block can be used (e.g., 504B shown in FIG. 5B). In another example, an integrated positioning and cutting guide block can be used for positioning and location.

In an example, after the positional burr cuts have been made to create engagement features, the tibial cutting block (e.g., 504A or 504B) can be placed in an unambiguous manner onto the tibia. The tibial cutting block (e.g., 504A or 504B) can be pinned in place with headed or non-headed pins to secure the guide during the subsequent bone-cutting operation. After a tibial cut has been made using the tibial cutting block (e.g., 504A or 504B), a tibial trial plate or an appropriate polyethylene insert trials of an appropriate thickness can be used to check for an appropriate knee joint extension or flexion gap. In an example, the tibial cutting block (e.g., 504A or 504B) can be removed prior to installing the tibial trial plate or polyethylene insert trial. In an example, a change to a slope angle can be done by repositioning the system. The system can be reused for a re-cutting procedure or a special re-cutting tibial cutting block can be used to increase the cutting depth or change the posterior slope of the tibial cut.

The implant geometry, specifically the femoral and polyethylene insert implant articulating surfaces, can be known to the CAS system via a database, and the ML rotation or AP rotation of the tibial components (tibial plate or polyethylene insert) can be aligned on the resected tibia. For example, the alignment can include a best fit position relative to the femoral implant so as not to create a mismatch of the femoral or tibial components during ambulation.

During extension of the knee, it is particularly important to align the articulating surface of the femoral and polyethylene inserts properly. Improper alignment can result in asymmetrical loading of the medial and lateral compartments, which can cause patient discomfort, sudden shifts in the knee position, or rapid rates of polyethylene wear. Asymmetrical loading can also cause the potential for cemented component loosening from the bone.

Figures 6A, 6B:
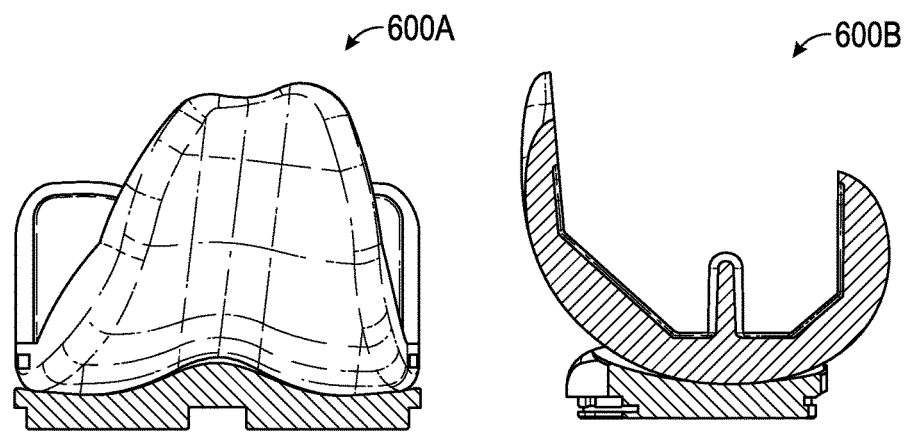
FIGS. 6A-B illustrate generally a properly placed femoral implant in accordance with some examples.

FIGS. 6A-B illustrate generally a properly placed femoral implant (e.g., 600A or 600B) in accordance with some examples. As shown in FIG. 6A, a ML cross-section, and as shown in FIG. 6B, an AP view, of a typical femoral implant in extension can be ideally located on the polyethylene insert. FIGS. 6A and 6B demonstrate a desired relationship between the femoral and tibial components when the leg is in the weight-bearing extension position.

Figure 7:
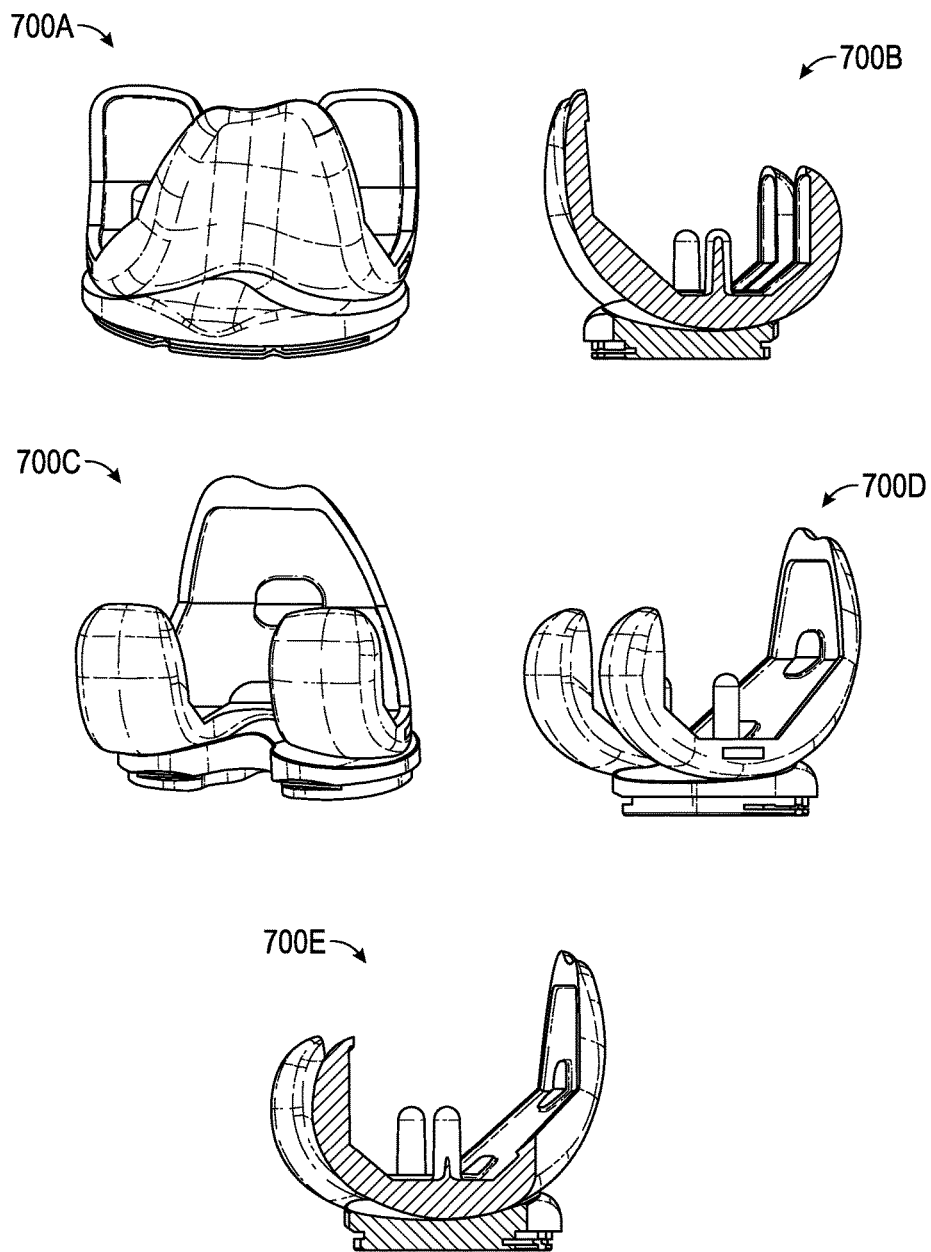
FIG. 7 illustrates generally improperly placed femoral implants in accordance with some examples.

FIG. 7 illustrates generally improperly placed femoral implants (e.g., 700A, 700B, 700C, 700D, or 700E) in accordance with some examples. Various examples in FIG. 7 show that any mal-rotation of the relative implant positions can cause localized areas of increased loading of the polyethylene insert and resultant abnormal rotation (either external or internal) of the tibial bone relative to the femur for the patient during ambulation, resulting in abnormal wear of the polyethylene insert and pain or discomfort for the patient.

Figure 8:
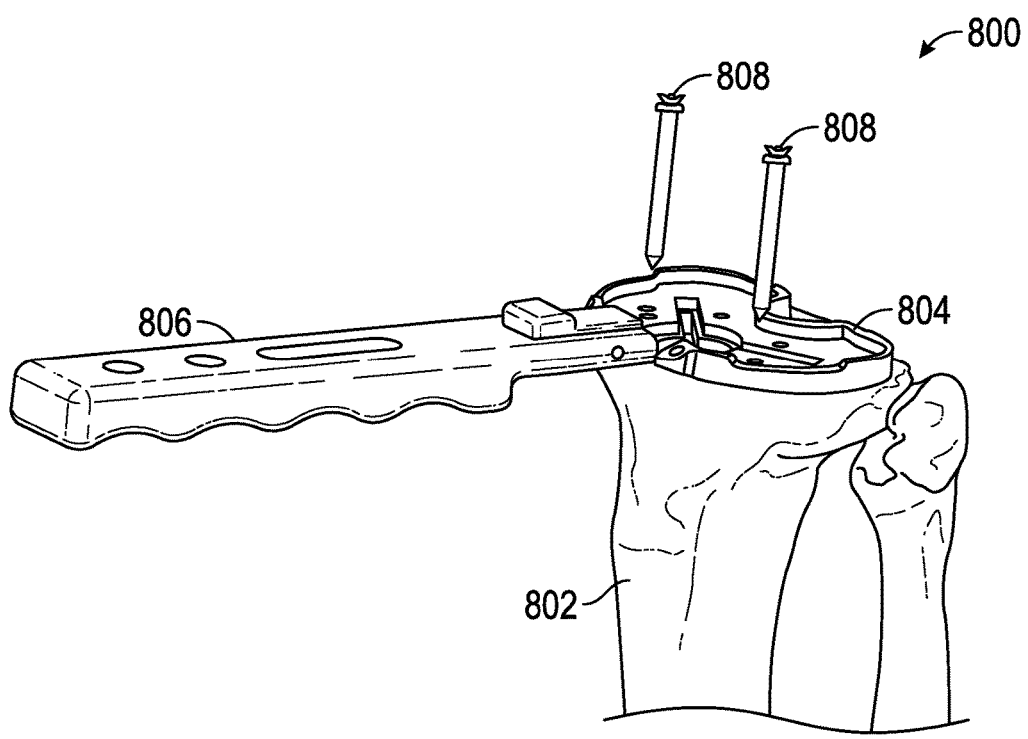
FIG. 8 illustrates generally a tibial plate trial and navigation positioner in accordance with some examples.

FIG. 8 illustrates generally a tibial plate trial 804 and navigation positioner 806 in accordance with some examples. To aid in minimizing the chance for tibial plate positioning errors, using a navigation system, a navigated positioner 806 can be attached to the tibial plate trial 804 prior to the punching of the tibia 802 for tibial keel in a tibial implant placement system 800. Pins 808 can be used to attach the tibial plate trial 804 to the tibia 802. In an example, the pins previously placed to secure the tibial cut guide can be used to minimize the chance for tibial plate positioning errors. For example, the navigated burr zones have been used to locate the cutting guide and to determine the pin position, and can be used in conjunction with a guiding device that interfaces with both the tibial plate trial and these pins. This can set ML rotational orientations of the tibial plate trial per the navigation plan. The AP location can be confirmed by placing the stylus onto a known reference on the tibial plate, where the null point of the tibial (e.g., polyethylene) insert location can be positioned to line up with the extension position of the femoral implant.

In yet another example, the most anterior burr zones can be made slightly deeper into the tibial plateau. This can allow the burr zones to still be visible after the tibial cut has been made. The burr zones can also be used to identify the anterior edge of the trial tibial plate for AP location. This, in combination with the ML or rotational placement dictated by the pin placement, can locate the trial tibial plate in an optimal position on the tibia and relative to the previously located femoral trial on the femur. As a result, the implants, and consequently the femur and tibia, can be in ideal positions to one another to maximize patient comfort and to maximize functioning of the knee and the implants.

In the examples described above and illustrated in FIGs. 1A-5B, some of the positioning components (e.g., anterior positioning block or distal positioning component) are discussed as involving multiple mating components that couple together during use to form a complete positioning component or guide. In some examples, a unitary positioning component is used that can be fabricated from deformable (e.g., spring-like) materials that will snap into engagement features machined into the bone. Applications of the discussed instrumentation and techniques may be modified in certain ways, such as unitary positioning components or multi-part positioning components, depending upon the requirements of the particular procedure or target joint (e.g., elbow, hip, shoulder, etc . . . ).

The examples described above may reference positioning components or cut guides by particular names that may indicate how the particular piece of instrumentation is used in the example procedure, such as the anterior positioning block). These specific names are used solely to provide additional clarity within the described example procedure. The positioning component concepts and related tools for creation of engagement features discussed are applicable to other procedures involving resection of bone or soft tissue within various anatomical locations.

Figure 9:
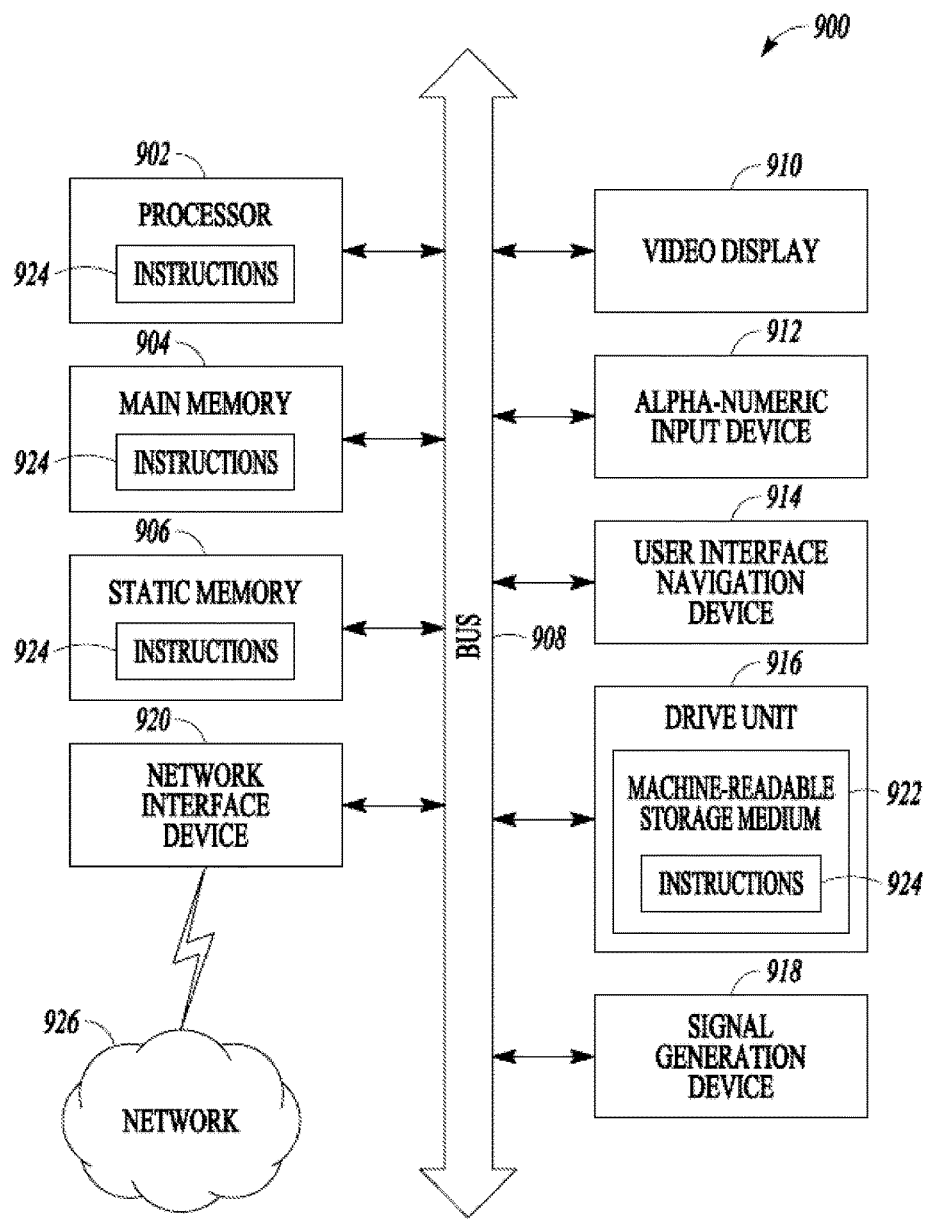
FIG. 9 is a block diagram that illustrates an example of a computer system within which instructions for causing the computer system to perform bone cut positioning can be executed in accordance with some examples.

FIG. 9 is a block diagram that illustrates an example of a block diagram of a machine in the form of a computer system 900 within which instructions, for causing the computer system to perform any one or more of the methods discussed herein, can be executed. In various embodiments, the machine can operate as a standalone device or can be connected (e.g., networked) to other machines. In a networked deployment, the machine can operate in the capacity of a server or a client machine in server-client network environment, or as a peer machine in a peer-to-peer (or distributed) network environment. The machine can be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (such as a central processing unit (CPU), a graphics processing unit (GPU), or both), a main memory 904 and a static memory 906, which communicate with each other via a bus 908. The computer system 900 can further include a video display unit 910 (such as a liquid crystal display (LCD) or a cathode ray tube (CRT)), an alpha-numeric input device 912 (such as a keyboard), a user interface (UI) navigation device (or cursor control device) 914 (such as a mouse), a disk drive unit 916, a signal generation device 918 (e.g., a speaker) and a network interface device 920.

The disk drive unit 916 includes a machine-readable storage medium 922 on which is stored one or more sets of instructions and data structures (e.g., software) 924 embodying or used by any one or more of the methods or functions described herein. The instructions 924 can also reside, completely or at least partially, within the main memory 904, static memory 906, or within the processor 902 during execution thereof by the computer system 900, the main memory 904 and the processor 902 also constituting machine-readable media. In an example, the instructions 924 stored in the machine-readable storage medium 922 include instructions causing the computer system 900 to determine a patient-specific model of the bone and using a computer controlled cutting instrument, prepare an engagement feature in the bone using the patient-specific model. The instructions 924 can also store the instructions 924 that cause the computer system 900 to create a virtual model to be used to prepare an engagement feature on a bone. The machine-readable storage medium 922 can further store the instructions 924 that cause the computer system 900 to operate a computer aided surgery (CAS) system.

While the machine-readable medium 922 is shown in an example embodiment to be a single medium, the term "machine-readable medium" can include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methods of the present invention, or that is capable of storing, encoding or carrying data structures used by or associated with such instructions. The term "machine-readable storage medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that can be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

In various examples, the instructions 924 can further be transmitted or received over a communications network 926 using a transmission medium. The instructions 924 can be transmitted using the network interface device 920 and any one of a number of well-known transfer protocols (e.g., HTTP). Examples of communication networks include a LAN, a WAN, the Internet, mobile telephone networks, plain old telephone (POTS) networks, and wireless data networks (e.g., Wi-Fi and WiMAX networks). The term "transmission medium" shall be taken to include any intangible medium that is capable of storing, encoding or carrying instructions for execution by the machine, and includes digital or analog communications signals or other intangible media to facilitate communication of such software.

Figure 10:
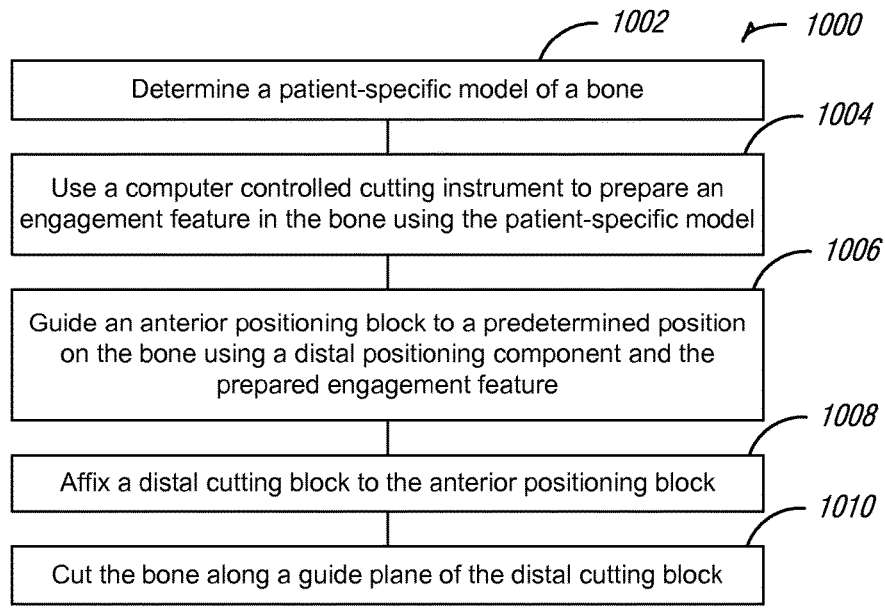
FIGS. 10-11 are flowcharts showing a method for operating a system for use in orthopedic surgery on a bone in accordance with some examples.

FIG. 10 is a flowchart showing a method 1000 for operating a system for use in orthopedic surgery on a bone in accordance with some examples. The method 1000 can include an operation 1002 to determine a patient-specific model of a bone and an operation 1004 to use a computer controlled cutting instrument to prepare an engagement feature in the bone using the patient-specific model. The method 1000 can include an operation 1006 to guide an anterior positioning block (e.g., anterior positioning block 204) to a predetermined position on the bone using a distal positioning component (e.g., distal positioning component 202) and the prepared engagement feature (e.g., engagement features 102). In an example, the distal positioning component can be attached to the anterior positioning block. The method 1000 can include removing the distal positioning component after the anterior positioning block is attached to the target bone.

The method 1000 can include an operation 1008 to affix a distal cutting block (e.g., distal cutting block 304) to the anterior positioning block. In an example, the distal cutting block can be affixed to the anterior positioning block after the distal positioning component is removed. The positions for affixing the distal cutting block and the distal positioning component can be overlapping. For example, when the distal cutting block and distal positioning component are affixed in overlapping positions, only one can be attached or affixed to the anterior positioning block at a time.

The method 1000 can include an operation 1010 to cut the bone along a guide plane of the distal cutting block. In an example, the method 1000 includes removing the distal cutting block after cutting the bone along the guide plane, attaching a 4-in-1 cutting block (e.g., 4-in-1 cutting block 406) to the anterior positioning block using a universal adapter (e.g., universal adapter 404), and cutting the bone along a guide plane of the 4-in-1 cutting block.

Figure 11:
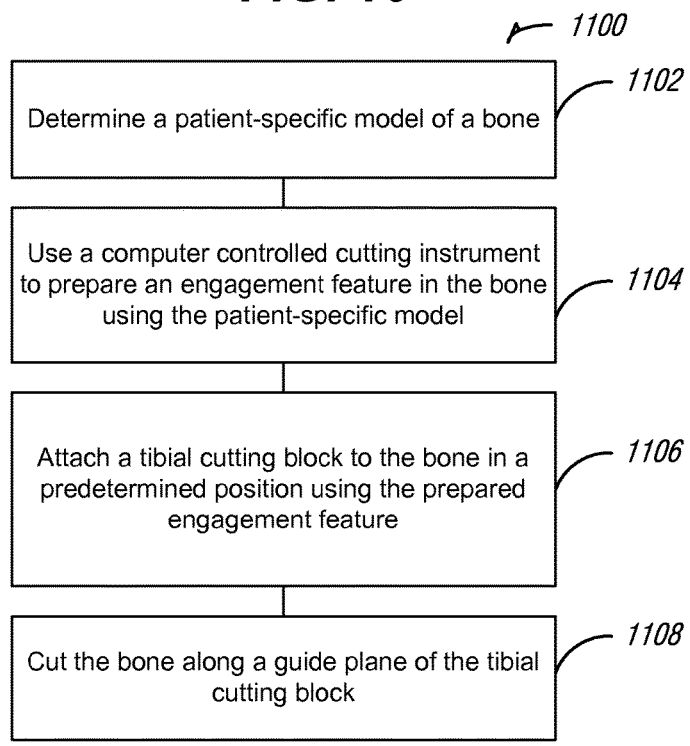

FIG. 11 is a flowchart showing a method 1100 for operating a system for use in orthopedic surgery on a bone in accordance with some examples. The method 1100 can include an operation 1102 to determine a patient-specific model of a bone and an operation 1104 to use a computer controlled cutting instrument to prepare an engagement feature in the bone using the patient-specific model. The method 1100 can include an operation 1106 to attach a tibial cutting block (e.g., tibial cutting block 504A or 504B) to the bone in a predetermined position using the prepared engagement feature. The method 1100 can include an operation 1108 to cut the bone along a guide plane of the tibial cutting block. The method 1100 can be used to place a tibial trial plate and re-cut the bone if needed. The tibial cutting block can be re-used to re-cut the bone or a new re-cutting tibial block can be used to re-cut the bone. In an example, after cutting and, if necessary, re-cutting, a polyethylene insert can be attached to the bone. In another example, a navigated positioner (e.g., navigated positioner 806) can be attached to a tibial trial plate (e.g., tibial trial plate 804) to determine an appropriate knee joint extension or flexion gap.

VARIOUS NOTES & EXAMPLES

Each of these non-limiting examples can stand on its own, or can be combined in various permutations or combinations with one or more of the other examples.

Example 1 includes the subject matter embodied by an orthopedic surgical device for use in operating on a target bone comprising: a primary positioning block, a secondary positioning component removably coupled to the primary positioning block, the secondary positioning component configured to: engage a prepared engagement feature machined into the target bone, and guide the primary positioning block to a predetermined position on a target bone, and a first cutting block configured to: removably couple to the primary positioning block, and guide a cutting tool to cut the target bone.

In Example 2, the subject matter of Example 1 can optionally include wherein the prepared engagement feature is created using a virtual model.

In Example 3, the subject matter of one or any combination of Examples 1-2 can optionally include wherein the virtual model includes a patient-specific virtual model of the target bone.

In Example 4, the subject matter of one or any combination of Examples 1-3 can optionally include further comprising a 4-in-1 cutting block removably coupled to the primary positioning block.

In Example 5, the subject matter of one or any combination of Examples 1-4 can optionally include wherein the 4-in-1 cutting block is coupled to the primary positioning block after the secondary positioning component is removed.

In Example 6, the subject matter of one or any combination of Examples 1-5 can optionally include wherein the 4-in-1 cutting block is configured to removably couple to the primary positioning block in a configuration at least partially overlapping a position of the secondary positioning component or the first cutting block.

In Example 7, the subject matter of one or any combination of Examples 1-6 can optionally include wherein the 4-in-1 cutting block is removably coupled to the primary positioning block using a universal adapter.

In Example 8, the subject matter of one or any combination of Examples 1-7 can optionally include wherein the 4-in-1 cutting block is further configured to guide a plurality of cuts.

In Example 9, the subject matter of one or any combination of Examples 1-8 can optionally include wherein the 4-in-1 cutting block is configured to guide the plurality of cuts when the primary positioning block and the universal adapter are removed.

In Example 10, the subject matter of one or any combination of Examples 1-9 can optionally include wherein the secondary positioning component and the first cutting block are configured to removably couple to the anterior positioning block in partially overlapping positions.

In Example 11, the subject matter of one or any combination of Examples 1-10 can optionally include wherein the secondary positioning component, the first cutting block, and the primary positioning block are not patient-specific.

In Example 12, the subject matter of one or any combination of Examples 1-11 can optionally include wherein the primary positioning block is an anterior positioning block, the secondary positioning component is a distal positioning component, and the first cutting block is a distal cutting block.

Example 13 includes the subject matter embodied by a system for preparing a bone in a joint for an implant, the system comprising: a computer controlled cutting instrument configured to prepare an engagement feature in the bone, a positioning fixture, configured to engage the prepared engagement feature, the positioning fixture comprising: a primary positioning block, and a secondary positioning component removably coupled to the primary positioning block, and a first cutting block configured to: removably couple to the primary positioning block, and guide a cutting tool to cut the bone.

In Example 14, the subject matter of Example 13 can optionally include a 4-in-1 cutting block configured to: removably couple to the primary positioning block using a universal adapter, and guide a second cutting tool to cut the bone.

In Example 15, the subject matter of one or any combination of Examples 13-14 can optionally include wherein the prepared engagement feature is created using a virtual model.

In Example 16, the subject matter of one or any combination of Examples 13-15 can optionally include wherein the bone is a femur.

In Example 17, the subject matter of one or any combination of Examples 13-16 can optionally include wherein the computer controlled cutting instrument is controlled by a computer aided surgery (CAS) system.

In Example 18, the subject matter of one or any combination of Examples 13-17 can optionally include wherein the primary positioning block is an anterior positioning block, the secondary positioning component is a distal positioning component, and the first cutting block is a distal cutting block.

Example 19 includes the subject matter embodied by a method for operating a system for use in orthopedic surgery on a bone, the method comprising: determining a patient-specific model of the bone, using a computer controlled cutting instrument to prepare an engagement feature in the bone using the patient-specific model, guiding a primary positioning block to a predetermined position on the bone using a secondary positioning component and the prepared engagement feature, affixing a first cutting block to the primary positioning block, and cutting the bone along a guide plane of the first cutting block.

In Example 20, the subject matter of Example 19 can optionally include wherein the secondary positioning component is attached to the primary positioning block and further comprising removing the secondary positioning component after the primary positioning block is attached to the target bone.

In Example 21, the subject matter of one or any combination of Examples 19-20 can optionally include wherein the first cutting block is affixed to the primary positioning block after the secondary positioning component is removed.

In Example 22, the subject matter of one or any combination of Examples 19-21 can optionally include removing the first cutting block after cutting the bone along the guide plane, attaching a 4-in-1 cutting block to the primary positioning block using a universal adapter, and cutting the bone along a guide plane of the 4-in-1 cutting block.

In Example 23, the subject matter of one or any combination of Examples 19-22 can optionally include wherein the primary positioning block is an anterior positioning block, the secondary positioning component is a distal positioning component, and the first cutting block is a distal cutting block.

In Example 24, the subject matter of one or any combination of Examples 1-23 can optionally include wherein the primary positioning block is created from a virtual model.

In Example 25, the subject matter of one or any combination of Examples 1-24 can optionally include wherein the secondary positioning component is created from a virtual model.

In Example 26, the subject matter of one or any combination of Examples 1-25 can optionally include wherein the first cutting block is created from a virtual model.

Example 27 includes the subject matter embodied by a method for operating a system for use in an orthopedic surgery on a bone, the method comprising: determining a patient-specific model of the bone, modeling virtual engagement features on the patient-specific model of the bone to fit an anterior/distal positioning fixture, the anterior/distal positioning fixture including an anterior positioning block and a distal positioning component, making engagement feature cuts on the bone using the virtual engagement features, affixing the physical anterior/distal positioning fixture to the bone using the engagement feature cuts, removing the distal positioning component from the bone, attaching a distal cutting block to the anterior positioning block, making a distal cut on the bone using the distal cutting block, removing the distal cutting block from anterior positioning block, attaching a 4-in-1 cutting block to the bone using a universal adapter and the anterior positioning block, removing the anterior positioning block and the universal adapter, making a plurality of cuts on the bone using the 4-in-1 cutting block, or attaching an implant aligned with the plurality of cuts.

Example 28 includes the subject matter embodied by a method for operating a system for use in an orthopedic surgery on a bone, the method comprising: determining a patient-specific model of the bone, modeling virtual engagement features on the patient-specific model of the bone to fit a tibial cutting block, making engagement feature cuts on the bone using the virtual engagement features, affixing a tibial cutting block to the bone with screws or pins using the engagement feature cuts, making a tibial cut on the bone using the tibial cutting block, removing the tibial cutting block, placing a tibial plate on the bone, attaching a navigated positioner to the tibial plate trial, determining if a re-cut is needed using the physical tibial plate on the bone, or attaching a polyethylene insert to the bone.

Example 29 includes the subject matter embodied by a system comprising computer assisted surgery software, an anterior distal positioning fixture including a distal positioning portion and an anterior positioning block, a distal cutting block, a universal adapter, or a 4-in-1 cutting block.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations.

What is claimed is:

1. A system for preparing a bone in a joint for an implant, the system comprising:

a computer-controlled cutting instrument configured to prepare an engagement feature in the bone, wherein preparing the engagement feature comprises:
  intraoperatively generating a virtual model of the bone, the virtual model comprising at least one implant component virtually positioned on the bone in a best fit position,
  creating one or more virtual burr zones on the virtual model of the bone, the one or more virtual burr zones corresponding to specific locations on the at least one implant component, and
  removing, using the computer-controlled cutting instrument, bone material within the one or more virtual burr zones, thereby preparing the engagement feature;
a positioning fixture, configured to engage the prepared engagement feature, the positioning fixture comprising:
  a primary positioning block, and
  a secondary positioning component removably coupled to the primary positioning block; and
a first cutting block configured to:
  removably couple to the primary positioning block, and
  guide a cutting tool to cut the bone.

2. The system of claim 1, further comprising:
a 4-in-1 cutting block configured to:
  removably couple to the primary positioning block using a universal adapter; and
  guide a second cutting tool to cut the bone.

3. The system of claim 1, wherein the bone is a femur.

4. The system of claim 1, wherein the computer-controlled cutting instrument is controlled by a computer aided surgery (CAS) system.

5. The system of claim 1, wherein the primary positioning block is an anterior positioning block, the secondary positioning component is a distal positioning component, and the first cutting block is a distal cutting block.

6. The system of claim 4, wherein the CAS system is configured to intraoperatively generate the virtual model of the bone and create the one or more virtual burr zones on the virtual model of the bone.

7. The system of claim 6, wherein the CAS system is further configured to instruct the computer-controlled cutting instrument to remove the bone material when a position of a cutting surface of the computer-controlled cutting device is positioned within the one or more virtual burr zones.

8. A system for preparing a bone in a joint for an implant, the system comprising:
a computer aided surgery (CAS) system configured to:
  intraoperatively generate a virtual model of a bone, the virtual model comprising at least one implant component virtually positioned on the bone in a best fit position,
  determine a location of an engagement feature on the virtual model of the bone, the one or more engagement features corresponding to specific locations on the at least one implant component, and
  create one or more virtual burr zones on the virtual model of the bone, the one or more virtual burr zones based upon the location of the engagement feature;
a computer-controller cutting instrument operably connected to the CAS system and configured to:
  receive instructions to remove bone material on the bone positioned within the one or more virtual burr zones, and
  prepare the engagement feature in the bone; and
a positioning fixture configured to engage the engagement feature.

9. The system of claim 8, wherein the positioning fixture comprises:
a primary positioning block; and
a second positioning component removably coupled to the primary positioning block and configured to engage at least a portion of the engagement feature.

10. The system of claim 9, further comprising a first cutting block configured to:
removably couple to the primary positioning block; and
guide a first cutting tool to cut at least a portion of the bone.

11. The system of claim 10, further comprising a multi-cut cutting block configured to:
removably couple to the primary positioning block; and
guide a second cutting tool to cut the bone.

12. The system of claim 11, further comprising a universal adapter configured to removably couple the multi-cut cutting block to the primary positioning block.

13. The system of claim 10, wherein the primary positioning block comprises an anterior positioning block, the secondary positioning component comprises a distal positioning component, and the first cutting block comprises a distal cutting block.

14. The system of claim 8, wherein the bone is a femur.

15. A system for preparing a bone in a joint for an implant, the system comprising:
a computer aided surgery (CAS) system configured to:
  intraoperatively generate a virtual model of a bone,
  overlay a virtual representation of an implant component on the virtual model of the bone,
  determine a location of at least one engagement feature on the virtual model of the bone, the location of the at least one engagement feature based upon specific locations of the virtual representation of the implant component as positioned on the virtual model of the bone, and
  create one or more virtual burr zones on the virtual model of the bone, the one or more virtual burr zones based upon the location of the at least one engagement feature;
a computer-controller cutting instrument operably connected to the CAS system and configured to:
  receive instructions to remove bone material on the bone positioned within the one or more virtual burr zones, and
  prepare the at least one engagement feature in the bone; and
a positioning fixture configured to be removably affixed to the bone via the at least one engagement feature.

16. The system of claim 15, wherein the positioning fixture comprises:
an anterior positioning block; and
a distal positioning component removably coupled to the anterior positioning block and configured to engage at least a portion of the at least one engagement feature.

17. The system of claim 16, further comprising a distal cutting block configured to:
removably couple to the anterior positioning block; and
guide a first cutting tool to cut at least a portion of the bone.

18. The system of claim 17, further comprising a multi-cut cutting block configured to:
removably couple to the anterior positioning block; and
guide a second cutting tool to cut at least a portion of the bone.

19. The system of claim 18, further comprising a universal adapter configured to removably couple the multi-cut cutting block to the anterior positioning block.

20. The system of claim 15, wherein the bone is a femur.

* * * * *